United States Patent [19]

Sramek

[11] 4,450,527

[45] May 22, 1984

[54] NONINVASIVE CONTINUOUS CARDIAC OUTPUT MONITOR

[75] Inventor: Bohumir Sramek, Irvine, Calif.

[73] Assignee: BoMed Medical Mfg. Ltd., Irvine, Calif.

[21] Appl. No.: 393,429

[22] Filed: Jun. 29, 1982

[51] Int. Cl.³ .................. G06F 15/42; H03K 13/02; A61B 5/02; A61B 5/04

[52] U.S. Cl. .................. 364/415; 364/416; 364/417; 128/693; 128/694; 128/670; 128/671; 128/720; 128/725; 128/734

[58] Field of Search .................. 364/415, 416, 417; 128/693, 694, 670, 671, 720, 725, 734

[56] References Cited

U.S. PATENT DOCUMENTS

| | | | |
|---|---|---|---|
| Re. 30,101 | 9/1979 | Kubicek et al. | 128/713 |
| 3,730,171 | 5/1973 | Namon | 128/713 |
| 3,835,839 | 9/1974 | Brown | 364/415 X |
| 3,835,840 | 9/1974 | Mount | 324/65 R X |
| 3,871,359 | 3/1975 | Pacela | 128/693 X |
| 3,882,851 | 5/1975 | Sigworth | 128/723 X |
| 3,994,284 | 11/1976 | Voelker | 364/575 X |
| 3,996,925 | 12/1976 | Djordjevich | 364/416 X |

*Primary Examiner*—Jerry Smith
*Assistant Examiner*—Allen MacDonald
*Attorney, Agent, or Firm*—Knobbe, Martens, Olsen & Bear

[57] ABSTRACT

The invention provides apparatus and methods for using the electrical bioimpedance measurements to monitor parameters associated with blood flow in a segment of body tissue. The invention eliminates the effect of respiration from the thoracic impedance as a function of time to provide a signal indicative of pulsatile thoracic impedance changes continuously. The pulsatile thoracic impedance signal is processed to produce signals indicative of the ventricular ejection time and the maximum rate of change of pulsatile thoracic impedance which are used in a microprocessor to calculate the volume of blood pumped per stroke according to an improved systolic upstroke equation.

14 Claims, 12 Drawing Figures

NONINVASIVE CONTINUOUS CARDIAC OUTPUT MONITOR

BACKGROUND OF THE INVENTION

This invention is generally related to apparatus and methods for measuring parameters associated with the flow of blood through a body segment. More particularly, this invention is related to apparatus and methods for monitoring cardiac output. Still more particularly, this invention is related to noninvasive apparatus and methods for continuously monitoring cardiac parameters.

Cardiac output is the volume of blood which the heart pumps in one minute and is one of the most important cardiovascular parameters. The cardiac output reflects the supply of oxygen and nutrients to tissue. Measurements of cardiac output provide invaluable clinical information for quanitifying the extent of cardiac dysfunction, indicating the optimal course of therapy, managing patient progress, and establishing check points for rehabilitation in a patient with a damaged or diseased heart, or one in whom fluid status control is essential. Exercise as well as pathological conditions of the heart and circulatory system will alter cardiac output; therefore, the measurement of cardiac output is useful both in rehabilitation and in critically ill patients.

Instrumentation currently in use for invasive and noninvasive measurement of cardiac output has several disadvantages. Cardiac output may be measured either invasively or noninvasively. The invasive techniques for measuring cardiac output involve penetration of the skin by a catheter, require complex instrumentation which must be operated by skilled personnel, and present a risk to the patient. Invasive techniques such as indicator dilution and thermal dilution allow only intermittent measurement of cardiac output since it is possible to obtain only one determination of cardiac output per injection in dilution methods.

The noninvasive techniques for measuring cardiac parameters include ballistocardiography, electrical impedance measurements, ultrasonics, phonocardiography and vibrocardiography. The instrumentation involved in present noninvasive techniques for measuring cardiac output is complex, expensive, inconvenient to use and requires highly trained operators. Existing electrical impedance instrumentation permits determination of cardiac output only during voluntary apnea, which means that the patient must hold his breath. Therefore, existing electrical impedance instrumentation is unsuitable for use with critically ill or unconscious patients.

Electrical bioimpedance measurements permit quanitifaction of blood flow as a result of changes in electrical conductivity of a body segment. The electrical impedance technique for measuring cardiac output is based upon changes in thoracic electrical impedance caused by cardiovascular activity. The change in impedance has several origins:

1. Cardiovascular activity causes pulsatile impedance changes. Approximately one-half of the pulsatile impedance change is related to volumetric changes of blood in the arteries as a result of arterial pressure compliance because blood is the most electrically conductive substance in the body. The other half of the pulsatile impedance change is caused by variation of the specific resistivity of blood as a function of blood velocity, which is related to the alignment of red blood cells.

2. Ventilation causes pulsatile impedance changes. In the thoracic region, the ventilation related impedance changes are directly proportional to the varying amount of air in the lungs while in the extremities the ventilation related impedance changes are caused by variation of the venus pool as a result of ventilation.

3. Edema and blood pooling cause nonpulsatile impedance changes.

The impedance changes listed as (1) above enter into the calculation for quanitification of cardiac output. The ventilation impedance changes (2) represent an unwanted background signal which must be suppressed to obtain accurate results.

The electrical impedance technique for measuring cardiac output has a significant advantage over the dilution methods, in addition to being noninvasive, in that the result of the measurement of the impedance change is the stroke volume, which is the volume of blood pumped per one heart contraction, which, when multiplied by heart rate, results in cardiac output. Therefore, stroke volume provides the clinician with beat-two-beat information on cardiac function. Indicator dilution methods determine average cardiac output only. However, the electrical impedance measurement technique has failed to gain wide acceptance since it has demonstrated a good correlation with invasive techniques only on healthy individuals. A strong deviation from expected values of cardiac output occurred in patients with pulmonary apnea or increased thoracic fluid content. The deviation is related to the mathematical structure of the equations used to calculate the stroke volume.

The first useful equation to quantify stroke volume from the cardiovascular impedance change was described by Nyboer, electrical impedance plethysmography, Charles C. Thomas, 1959. Myboer's equation is:

$$SV = \frac{RL^2}{Z_0^2} \Delta Z$$

which uses the systolic downstroke extrapolation method on a graph of the thoracic impedance as a function of time to determine the cardiovascular impedance change during a heartbeat. R is the resistivity of blood of the subject, L is the average distance between sensing electrodes attached to the subject, $\Delta Z$ is the cardiovascular impedance change, and $Z_o$ is the base electrical impedance of the thorax. Typical magnitudes of the thoracic variables for a healthy subject are $Z_o=30$ ohms, R=150 ohm centimeters, L=30 centimeters, and $\Delta Z=30$ milliohms. Since ventilation impedance changes are typically an order of magnitude larger than the cardiovascular impedance changes, all measurements using Nyboer's method have to be performed during voluntary apnea. Therefore, Nyboer's method is currently used in peripheral applications only.

Kubicek et al, "The Minnesota Impedance Cardiography-Theory and Applications", *Biochem. Eng.* 9: 410, 1974, describe an improved equation for the calculation of stroke volume. Kubicek introduced the product of two cardiovascular variables, ventricular ejection time T and the maximum rate of impedance change $\Delta Z/sec$, in place of a single cardiovascular variable, $\Delta Z$ used in Nyboer's equation. The maximum rate of impedance change can be derived either from the graphical extrapolation of systolic upstroke impedance change to maintain a rate of impedance change in one second or from the maximum value of electronically derived first derivative of impedance change. Kubicek's equation is:

$$SV = \frac{RL^2}{Z_o^2} T (\Delta Z/sec)$$

where SV=stroke volume, R is the specific resistivity of blood, L is the distance between sensing electrodes, $Z_o$ is the base electrical impedance, T is the ventricular ejection time, and $\Delta Z$/sec is the maximum rate of impedance change.

In spite of the clear advantage of being capable of noninvasive cardiac output determination, electrical bioimpedance measurements have not gained wide spread use in thoracic measurements for the following reasons:

1. Good correlation against other techniques could be demonstrated only on healthy individuals;
2. Calculated cardiac output of patients with increased thoracic fluid content was much higher than the expected value;
3. There are unresolved questions about the influence of hematocrit on the accuracy of calculation of cardiac output;
4. The determination of cardiac output could be performed only intermittently with the subject in voluntary apnea;
5. The electrodes used with prior art devices are not suitable for long term monitoring; and
6. The existing instrumentation is high in cost and very complex, requiring skilled operators.

Therefore, there is a need for a system for monitoring cardiac output parameters which may be used continuously, is simple to operate, is safe for both the subject and operators, has the versatility to measure and display several cardiovascular variables for every heartbeat and which has relatively low initial cost and low operating costs.

SUMMARY OF THE INVENTION

The present invention overcomes the deficiencies associated with prior art devices and methods for using bioimpedance measurements to monitor cardiac output parameters. The invention provides a noninvasive apparatus and method using the principle of electrical bioimpedance to continuously monitor cardiac output. A small, constant amplitude, high-frequency electrical current flowing parallel to the spine develops a voltage across the thorax. The voltage across the thorax is proportional to the thoracic electrical impedance. The dimensions of the thorax, thoracic electrical impedance, ventricular ejection time, and the maximum rate of impedance change are parameters used in an improved systolic upstroke equation to calculate the stroke volume. Cardiac output is obtained by multiplying the stroke volume by the heart rate.

The invention utilizes pregelled spot electrodes to facilitate continuous monitoring of cardiac output. The invention is simple to operate in that the operator needs only to attach the electrodes to the patient, turn the power on, enter the thoracic dimensions into the system, and select the desired variable to be displayed and monitored.

Cardiac output parameters are monitored by producing an electrical signal indicative of the thoracic impedance as a function of time and eliminating the effects of respiration from the thoracic impedance signal to produce a pulsatile impedance signal indicative of changes in thoracic impedance due to cardiovascular activity as a function of time. By electrically processing the thoracic impedance signal to eliminate the effects of respiration from the signal, the invention overcomes the deficiencies of prior art devices which require measurement of thoracic impedance during voluntary apnea. The electrical signal indicative of the pulsatile thoracic impedance is processed to determine the maximum rate of change of the pulsatile impedance signal. A microprocessor is programmed to use the thoracic base impedance, the ventricular ejection time, the maximum rate of change of pulsatile impedance, and the average distance between upper and lower sensing electrodes to produce signals indicative of stroke volume. The results of calculation can be digitally printed on a printer or may be displayed on a visual display to indicate the base thoracic impedance, the ventricular ejection time, the maximum rate of impedance change, the stroke volume, the heart rate, and the cardiac output.

DESCRIPTION OF THE PREFERRED EMBODIMENT

The invention may be used to monitor blood flow in any segment of tissue, however the following description refers to monitoring thoracic cardiovascular activity in order to provide a complete description of the new apparatus and method.

Figures 1A, 1B:
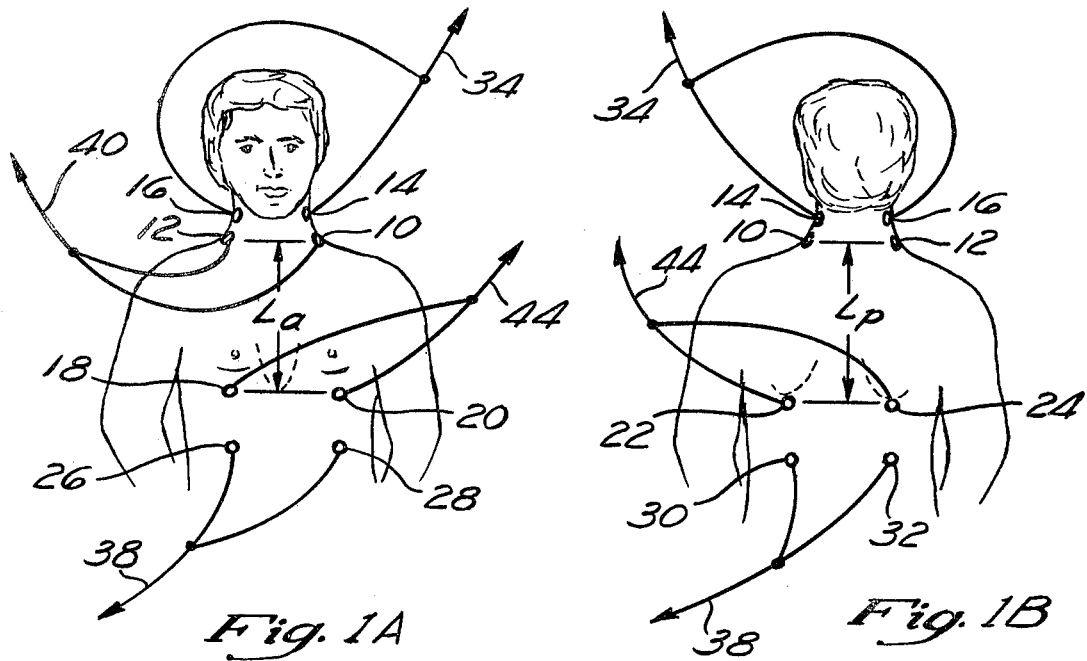
FIGS. 1A and 1B illustrate electrode placement to monitor cardiac output of a patient according to the invention.

A continuous cardiac output monitor according to the invention uses an array of spot electrodes on the patient as shown in FIG. 1. In a typical application, a pair of upper sensing electrodes 10 and 12 are attached to the patient's neck on opposite sides thereof at the intersections of the line encircling the root of the neck with the frontal plane. A pair of upper current injecting electrodes 14 and 16 are attached to the patient's neck approximately 3 to 5 centimeters above the upper sensing electrodes 10 and 12, respectively. A pair of lower thoracic anterior sensing electrodes 18 and 20 are placed at the intercostal space at each midclavicular line at the xiphoid process level. A pair of posterior sensing electrodes 22 and 24 shown in FIG. 1B are placed at the same level as the anterior sensing electrodes 18 and 20 at the intercostal space at the midscapular line. Referring again to FIG. 1A, a pair of lower current injecting electrodes 26 and 28 are located approximately 4 to 6 centimeters below the lower thoracic anterior sensing electrodes 18 and 20, respectively. Referring again to FIG. 1B, a pair of lower injecting electrodes 30 and 32 are attached to the patient approximately 4 to 6 centimeters below the posterior sensing electrodes 22 and 24. All of the electrodes 10, 12, 14, 16, 18, 20, 22, 24, 26, 28, 30, and 32 are preferably spot electrodes which have been pregelled.

Figure 2:
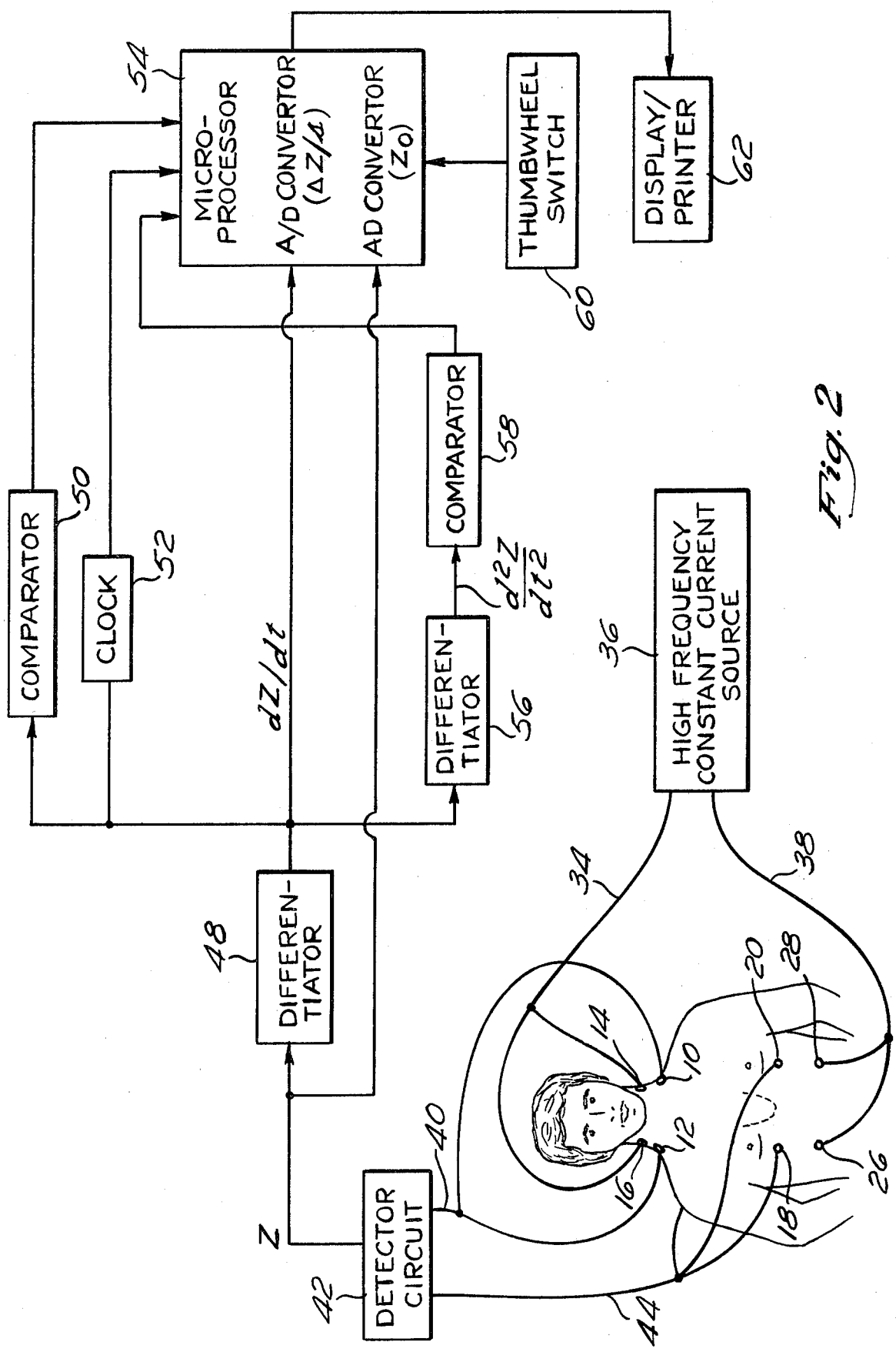
FIG. 2 is a block diagram of the electrical circuitry of the invention.

Referring to FIGS. 1A, 1B, and 2, a conductor 34 connects the upper injection electrodes to a current source 36, which preferably produces a high-frequency, constant amplitude current output. A conductor 38 connects both the anterior lower injection electrodes 26 and 28 and the posterior lower injection electrodes 30 and 32 to the current source 36. The frequency of the output of the current source 36 should be high enough to preclude any interference with proper functioning of the electrical systems within the human body. In a preferred embodiment of the invention, the current source 36 outputs a signal having an effective value of approximately 2.5 mA and a frequency of 70 kHz. A current source suitable for practicing the present invention is described in applicant's U.S. patent application entitled Constant Magnitude, High-Frequency Current Source, Ser. No. 06/393371, filed June 26, 1982.

A conductor 40 connects the upper sensing electrodes 10 and 12 to a detector circuit 42. A conductor 44 connects the lower thoracic anterior sensing electrodes 18 and 20 and the posterior sensing electrodes 22 and 24 to the detector circuit 42.

A noninvasive continuous cardiac output monitor according to the invention utilizes a modified systolic upstroke equation $$SV = \frac{V_{ept}}{Z_o} T (\Delta Z/\text{sec})$$

to calculate the stroke volume. $V_{ept}$ is the physical volume of electrically participating thoracic tissue in milliliters, and the other variables in the equation are the same as those defined in connection with Kubicek's systolic upstroke equation discussed hereinabove. The volume of electrically participating tissue is a function of the thoracic volume, which approximates that of a cyliner $$V_{ept} = \frac{C^2 L}{4\pi K}$$

Where C is the thoracic circumference; L is the average of the lines $L_a$ and $L_p$, shown in FIGS. 1A and 1B respectively and which are distances between the lines through the center of the upper sensing electrodes 10 and 12 and the lower sensing electrodes 18 and 20 and 22 and 24; and K is a ratio constant approximately in the range 2.6 to 2.8 for a typical C/L ratio of about 3 for which the equation reduces to $$V_{ept} = \frac{L^3}{4.25}$$

Figure 3:
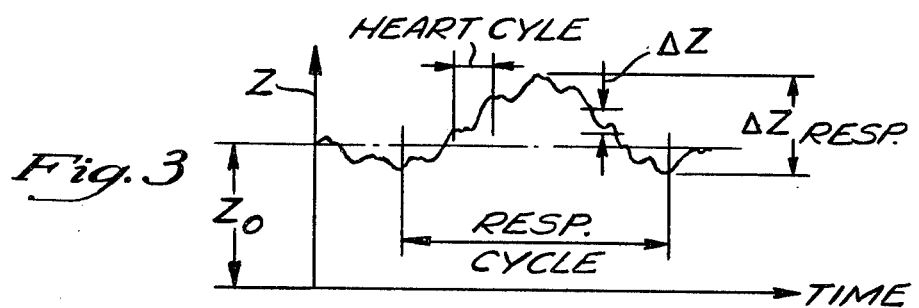
FIG. 3 is a graph of thoracic impedance as a function of time during normal respiration.

Referring to FIG. 3, the graph illustrates typical variations in thoracic impedance due to respiratory and cardiovascular activity as a function of time. The average of the thoracic impedance is $Z_o$. The variation of thoracic impedance due to respiratory activity is $\Delta Z_{resp}$; and $\Delta Z$ indicates variations of Z due to cardiovascular activity. As the graph of FIG. 3 indicates, $\Delta Z_{resp}$ is much greater than $\Delta Z$ while the frequency of $\Delta Z$ is about four times the frequency of $Z_{resp}$.

The output signal, of the detector circuit 42 represents the thoracic impedance as a function of time. The circuitry of FIG. 2 processes the thoracic impedance signal to obtain values for use in the modified systolic upstroke equation to monitor cardiovascular activity on a continuous basis.

Figure 5:
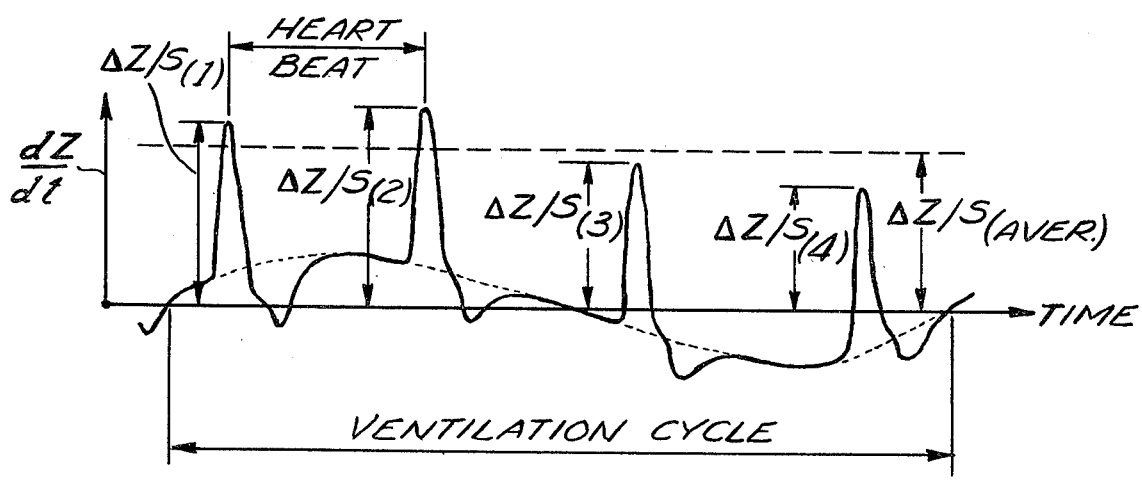
FIG. 5 is a graph of the first derivative of thoracic impedance as a function of time over a period of four heartbeats.

The suppression of the effects of ventilation is depicted in FIG. 5. FIG. 5 shows the actual waveform of the first derivative of the impedance signal, including the effects of ventilation, as the signal emerges from the output terminal of the differentiation 48 (FIG. 2). The signal shown in FIG. 5 is supplied to the analog to digital (A/D) converter of the microprocessor 54. The microprocessor 54 measures the maximum positive value of the dZ/dt waveform ($\Delta Z$/sec, FIG. 4C) at the time T1 (FIG. 4F), provided to the microprocessor 54 from the digital image (FIG. 4F) of the second derivative ot he impedance signal (FIG. 4E) for every heartbeat. Referring to FIG. 5, the microprocessor 54 will determine in four consecutive heartbeats the following $\Delta Z$/sec magnitudes:

$$\Delta Z/\text{sec}_{(1)},\ \Delta Z/\text{sec}_{(2)},\ \Delta Z/\text{sec}_{(3)};\ \text{and}\ \Delta Z/\text{sec}_{(4)}.$$

Applying the sliding arithmetic average of the last four heartbeats, the microprocessor 54 will calculate the average value of $\Delta Z/\text{sec}_{(AVER)}$, which then enters the calculation of stroke volume.

$$\Delta Z/\text{sec}_{(AVER)} = \frac{\Delta Z/\text{sec}_{(1)} + \Delta Z/\text{sec}_{(2)} + \Delta Z/\text{sec}_{(3)} + \Delta Z/\text{sec}_{(4)}}{14}.$$

A comparator 50 receives the signal dZ/dt output from the differentiator 48 and functions as a zero-crossing detector to provide a constant logic one output voltage when the signal dZ/dt is positive and a logic zero output when the signal dZ/dt is negative. Thus, the comparator 50 produces in response to dZ/dt a digital signal which is high when dZ/dt is positive and low when dZ/dt is negative. FIG. 4D is a graph of the digital representation of dZ/dt.

Figure 4A:
FIG. 4A is a grap representing an electrocardiogram signal.
Figure 4B:
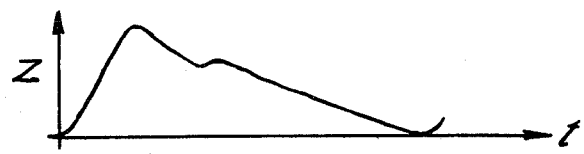
FIG. 4B is a graph of changes in thoracic impedance due to cardiovascular activity as a function of time.
Figure 4C:
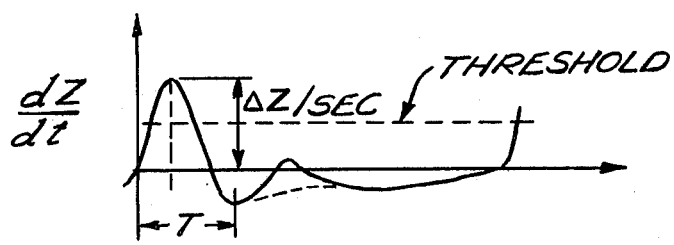
FIG. 4C is a graph of the first derivative of the graph of FIG. 4B.
Figure 4D:
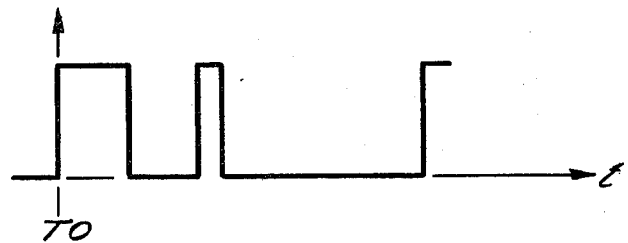
FIG. 4D is a digital representation of the graph of FIG. 4C.
Figure 4E:
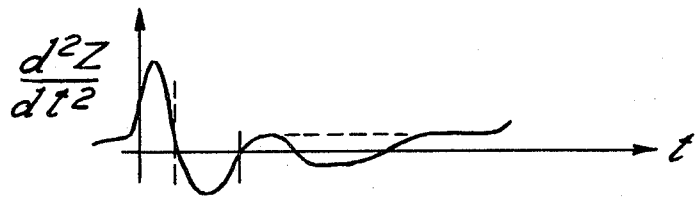
FIG. 4E is a graph of the second derivative of the graph of FIG. 4B.
Figure 4F:
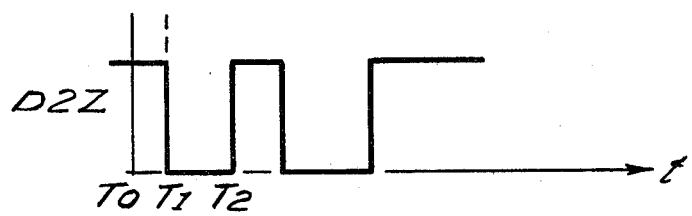
FIG. 4F is a digital representation of the graph of FIG. 4D.
Figure 4G:
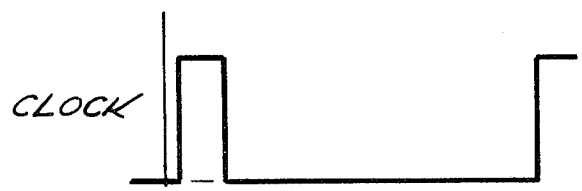
FIG. 4G is a representation of the signal from the apparatus clock.

The clock for the apparatus is determined in the clock circuit 52, the output of which is shown in FIG. 4G, and which is obtained in the digital form from the dZ/dt waveform (FIG. 4C) when the waveform crosses the positive D.C. threshhold.

Referring to FIGS. 2 and 4A, an electrocardiogram signal indicates the initiation of the systolic portion of a heartbeat, which determines the zero reference point for the time lines in FIGS. 4A–4F.

Referring to FIG. 4C, the ventricular ejection time T used in the calculation of the cardiac output is the time between the beginning of systolic contraction (time $T_0$) to the closure of the aortic valve (time $T_2$). The Time $T_2$ corresponds to the first negative minimum of dZ/dt waveform.

Obviously, the functions of the differentiator 48, the comparator 50, the clock 52, the differentiator 56, and the comparator 58 could be performed by software within the microprocessor 54.

A second differentiator 56 receives the output of the differentiator 48 and produces an output signal, shown in FIG. 4E, which represents the second derivative, $d^2Z/dt^2$, of the pulsatile thoracic impedance. A comparator 58 connected to the differentiator 56 digitizes $d^2Z/dt^2$ in a manner similar to that in which the comparator 50 digitizes the $dZ/dt$ signal. The output of the comparator 58 is a digital signal which is high when $d^2Z/dt^2$ is positive and low when $d^2Z/dt^2$ is negative.

The digital representation of the second derivative of the pulsatile thoracic impedance function is shown in FIG. 4F. The modified systolic upstroke equation used to calculate cardiac output utilizes the maximum value of the first derivative of the pulsatile impedance signal to calculate the stroke volume for each heartbeat. As shown in FIG. 4C, the absolute maximum value of the first derivative of the pulsatile thoracic impedance is the first maximum which occurs after initiation of the systolic portion of the heartbeat. Referring to FIG. 4E, the second derivative of the pulsatile thoracic impedance has a negative-going zero-crossing at the time at which the first derivative exhibits the absolute maximum value. In FIG. 4F, the first negative-going pulse edge in the digital representation of the second derivative of the pulsatile thoracic impedance occurs at the time at which the first derivative of the pulsatile thoracic impedance exhibits the maximum value. Therefore, the microprocessor is programmed to read the value of the first derivative of the pulsatile thoracic impedance at the occurrence of the first negative-going pulse edge after initiation of the systolic portion of each heartbeat.

Thus, the signals input to the microprocessor 54 are the thoracic impedance from the detector circuit 42; the first derivative of the pulsatile thoracic impedance from the differentiator 48; the time interval between the first two positive going zero-crossings of the first derivative of the pulsatile thoracic impedance, which is the ventricular ejection time, from the comparator 50; and the digital representation of the second derivative of the pulsatile thoracic impedance. The microprocessor 54 has included therein analog to digital converters to enable the microprocessor 54 to process the analog signals from the detector circuit 42 and the differentiator 48. A thumb wheel switch 60 permits entry of the value of L needed to determine the volume of the electrically participating tissue. A display 62, which may be a digital readout display or a digital printer, provides means for an operator to read values of the various cardiac output parameters for which the microprocessor is programmed to compute. Typical values for cardiac parameters output by the display 62 are $Z_o=31$ ohms, T=0.39 sec, $\Delta Z/\text{sec}=0.99$ ohm/sec, SV=74 ml, heart rate, HR=69/min. and cardiac output=5.1 liters/min.

Although the invention is described with reference to a specific preferred embodiment, modifications within the scope of the invention may be apparent to those skilled in the art. Therefore, the true scope of the invention is understood to be determined by the appended claims.

What is claimed is:

1. Noninvasive apparatus for continuously monitoring cardiac output of a patient during normal respiratory functions, comprising:
   means for producing an electrical signal indicative of thoracic impedance as a function of time;
   means for eliminating effects of respiration from the thoracic impedance signal to produce a pulsatile impedance signal indicative of changes in thoracic impedance due to cardiovascular activity as a function of time;
   means for processing the pulsatile impedance signal to produce a signal indicative of the maximum rate of change thereof as a function of time;
   means for processing the pulsatile impedance signal to produce a signal indicative of ventricular ejection time; and
   computing means, responsive to the ventricular ejection time signal and to the maximum rate of change of pulsatile impedance signal, for producing a signal indicative of stroke volume.

2. The apparatus defined in claim 1, additionally comprising:
   means for determining the heart rate; and
   computing means for determining from said stroke volume and said heart rate, cardiac output.

3. Apparatus according to claim 1 wherein said means for eliminating the effects of respiration from the thoracic impedance signal includes means for averaging the maximum rate of the thoracic impedance over a predetermined number of heartbeats of the patient.

4. Apparatus according to claim 1, 2 or 3 wherein said means for producing an electrical signal indicative of thoracic impedance comprises:
   a current source having a high-frequency constant amplitude electrical current output;
   injector electrode means for injecting the output of said current source into the thorax of the patient, said injector electrode means including a plurality of spot electrodes; and
   sensor electrode means for sensing electrical current flow through the thorax of the patient, said sensor electrode means including an array of spot electrodes.

5. Apparatus according to claim 1, 2 or 3 wherein said means for processing the pulsatile impedance signal to produce the signal indicative of the maximum rate of change of the pulsatile impedance signal includes:
   first differentiator circuit means for producing a signal indicative of the first derivative of the pulsatile impedance signal;
   second differentiator circuit means, connected to the output of said first differentiator circuit means, for producing a signal indicative of the second derivative of the pulsatile impedance signal; and
   comparator means for producing an output indicative of the zero-crossings of the signal indicative of the second derivative of the pulsatile impedance signal to indicate the maximum value of the first derivative of the pulsatile impedance signal after initiation of a heart beat.

6. Apparatus according to claim 5 wherein said means for processing the pulsatile impedance signal to produce the ventricular ejection time signal includes:
   second comparator means, connected to said first differentiator circuit means, for producing an output indicative of the zero-crossings of the first derivative of the pulsatile impedance signal; and
   clock means for measuring the time interval between two consecutive heartbeats to determine heart rate.

7. Apparatus according to claim 1, 2 or 3 further including:

first differentiator circuit means for producing a signal indicative of the first derivative of the pulsatile impedance signal;

means for producing a first digital logic signal responsive to the first derivative of the pulsatile impedance signal wherein a logic high represents positive values of the first derivative of the pulsatile impedance signal and a logic low represents negative values of the first derivative of the pulsatile impedance signal;

second differentiator circuit means connected to the output of said first differentiator circuit means for producing a signal indicative of the second derivative of the pulsatile impedance signal;

means for producing a second digital logic signal responsive to the second derivative of the pulsatile impedance signal wherein a logic high represents positive values of the second derivative of the pulsatile impedance signal and a logic low represents negative values of the second derivative of the pulsatile impedance signal; and means for determining the value of the first derivative of the pulsatile impedance signal at the first negative-going pulse edge in the second digital logic signal after initiation of a heartbeat.

8. Apparatus according to claim 7 further including:
means for measuring the time interval between the first positive going zero-crossing in the first derivative digital logic signal and the first positive going zero-crossing in the second derivative logic signal after initiation of a heartbeat.

9. A noninvasive method for continuously monitoring cardiac output of a patient during normal respiratory functions, comprising the steps of:
producing an electrical signal indicative of the thoracic impedance of the patient as a function of time;
eliminating the effects of respiration from the thoracic impedance signal, thereby producing a pulsatile impedance signal indicative of changes in thoracic impedance cardiovascular activity as a function of time;
processing the pulsatile impedance signal to produce a signal indicative of the maximum rate of change thereof;
processing the pulsatile impedance signal to produce a signal indicative of ventricular ejection time; and
computing a signal indicative of cardiac output as a function of the maximum rate of change of the pulsatile impedance signal and as a function of the signal indicative of ventricular ejection time.

10. A method according to claim 9 wherein producing an electrical signal indicative of thoracic impedance as a function of time further includes the steps of:
producing a high-frequency, constant amplitude electrical current;
injecting the high-frequency, constant amplitude electrical current into the thorax of the patient; and
sensing electrical current flow through the thorax of the patient.

11. A method according to claim 9 wherein the step of processing the pulsatile impedance signal to produce a signal indicative of the maximum rate of change of the pulsatile impedance signal includes the steps of:
differentiating the pulsatile impedance signal to produce a signal indicative of the first derivative thereof;
differentiating the signal indicative of the first derivative of the pulsatile impedance signal to produce a signal indicative of the second derivative thereof; and
producing a signal indicative of the zero-crossings of the signal indicative of the second derivative of the pulsatile impedance signal to indicate the time of occurrence of the first maximum value and first minimum value of the first derivative of the pulsatile impedance signal occurring after initiation of the systolic portion of a heartbeat.

12. A method according to claim 11 wherein the step for processing the pulsatile impedance signal to produce the ventricular ejection time signal includes the steps of:
producing an output signal indicative of the zero-crossings of the first derivative of the pulsatile impedance signal; and
measuring the time interval between the first positive going zero-crossing of the first derivative of the pulsatile impedance signal and the first positive going zero-crossing of the second derivative of the pulsatile impedance signal after initiation of the systolic portion of a heartbeat.

13. A method according to claim 10, further including the steps of:
producing a signal indicative of the first derivative of the pulsatile impedance signal;
producing a first digital logic signal responsive to the first derivative of the pulsatile impedance signal;
producing a signal indicative of the second derivative of the pulsatile impedance signal;
producing a second digital logic signal responsive to the second derivative of the pulsatile impedance signal; and
determining the value of the first derivative of the pulsatile impedance signal at the first negative-going pulse edge in the second digital logic signal after initiation of the systolic portion of a heartbeat.

14. A method according to claim 13 further including the step of measuring the time interval between the first positive going zero-crossing in the first digital logic signal and the first positive going zero-crossing of the second digital logic signal after initiation of the systolic portion of a heartbeat to determine the ventricular ejection time.

* * * * *

UNITED STATES PATENT AND TRADEMARK OFFICE
CERTIFICATE OF CORRECTION

PATENT NO. : 4,450,527
DATED : May 22, 1984
INVENTOR(S) : Bohumir Sramek

It is certified that error appears in the above-identified patent and that said Letters Patent are hereby corrected as shown below:

Column 4, Line 29, "grap" should be ---graph---.

Column 5, Line 28, "June 26, 1982" should be ---June 29, 1982--- .

Column 6, Line 25 "ot he" should be ---of the--- .

Signed and Sealed this

Fourteenth Day of May 1985

[SEAL]

Attest:

DONALD J. QUIGG

Attesting Officer

Acting Commissioner of Patents and Trademarks